US011970820B2

(12) United States Patent
Chen

(10) Patent No.: US 11,970,820 B2
(45) Date of Patent: Apr. 30, 2024

(54) COTTON RECYCLING

(71) Applicant: BOARD OF REGENTS, THE UNIVERSITY OF TEXAS SYSTEM, Austin, TX (US)

(72) Inventor: Jonathan Y. Chen, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 17/981,769

(22) Filed: Nov. 7, 2022

(65) Prior Publication Data

US 2023/0062813 A1 Mar. 2, 2023

Related U.S. Application Data

(62) Division of application No. 16/307,311, filed as application No. PCT/US2017/036695 on Jun. 9, 2017, now Pat. No. 11,525,214.

(60) Provisional application No. 62/347,819, filed on Jun. 9, 2016.

(51) Int. Cl.
| | |
|---|---|
| *D21H 11/20* | (2006.01) |
| *A61L 15/28* | (2006.01) |
| *C08B 16/00* | (2006.01) |
| *C08L 1/02* | (2006.01) |
| *D01G 11/00* | (2006.01) |
| *D21H 11/12* | (2006.01) |
| *D21H 11/16* | (2006.01) |
| *D21H 27/00* | (2006.01) |
| *B82Y 5/00* | (2011.01) |
| *B82Y 30/00* | (2011.01) |

(52) U.S. Cl.
CPC .............. *D21H 11/20* (2013.01); *A61L 15/28* (2013.01); *C08B 16/00* (2013.01); *C08L 1/02* (2013.01); *D01G 11/00* (2013.01); *D21H 11/12* (2013.01); *D21H 11/16* (2013.01); *D21H 27/00* (2013.01); *B82Y 5/00* (2013.01); *B82Y 30/00* (2013.01); *C08L 2207/20* (2013.01); *D10B 2201/02* (2013.01)

(58) Field of Classification Search
CPC ..................................................... D21H 11/20
See application file for complete search history.

(56) References Cited

U.S. PATENT DOCUMENTS

| | | | |
|---|---|---|---|
| 7,709,089 B2 | 5/2010 | Fushitani et al. | |
| 8,691,520 B2 | 4/2014 | Andreescu et al. | |
| 9,296,829 B2 | 3/2016 | Isogai et al. | |
| 2009/0220560 A1 | 9/2009 | Wan et al. | |
| 2011/0287245 A1* | 11/2011 | Shamei | D06M 23/08 428/221 |
| 2016/0130368 A1 | 5/2016 | Varma et al. | |
| 2016/0369456 A1 | 12/2016 | Flynn et al. | |

FOREIGN PATENT DOCUMENTS

| | | |
|---|---|---|
| CN | 101307563 B | 9/2010 |
| WO | 2015/077807 A1 | 6/2015 |

OTHER PUBLICATIONS

International Search Report and Written Opinion dated Sep. 6, 2017, from International Application No. PCT/US2017/036695, 9 pages.
Isogai, A. et al., "TEMPO-oxidized cellulose nanofibers," Nanoscale, 2011, 3:71-85.
Rodionova, G. et al. "TEMPO-Oxidized cellulose nanofiber films: effect of surface morphology on water resistance," Cellulose, 2012, 19:1115-1123.
Saito, T. et al. "Cellulose nanofibers prepared by TEMPO-mediated oxidation of native cellulose," Biomacromolecules, 2007, 8:2485-2491.

* cited by examiner

*Primary Examiner* — Shaojia A Jiang
*Assistant Examiner* — Everett White
(74) *Attorney, Agent, or Firm* — Meunier Carlin & Curfman LLC

(57) ABSTRACT

Cellulose materials and methods of making the cellulose materials are described herein. The method can include contacting a cotton fabric with an oxidizing system to obtain an oxidized cotton material and processing the oxidized cotton material to form the cellulose material. The oxidizing system can include an aqueous mixture of a N-oxyl compound and a hypochlorite compound. During oxidation, the pH of the aqueous mixture can be maintained at from 8.5 to 11. Cellulose products can be formed from the cellulose materials. For example, the cellulose products can be used to form a packaging material, a biomedical device or implant, a drug delivery material, a fiber, a textile material, a template for electronic components, or a separation membrane. Methods of making the cellulose product include dissolving or suspending an active ingredient in a medium comprising the cellulose material.

14 Claims, No Drawings

COTTON RECYCLING

FIELD OF THE DISCLOSURE

This disclosure relates generally to recycling cotton fibers, more particularly, to recycling cotton fabrics to provide functional cellulose materials.

BACKGROUND OF THE DISCLOSURE

Barrier properties of materials are important in reducing the penetration of moisture, oxygen, grease, aromas and, in some cases, bacteria. For example, exclusion of oxygen and moisture from packaged foods retards product spoilage. In certain applications, such as packaging of detergents, cleaners, fertilizers and the like, it is important that the packaging material prevents the odors from spreading outside. In other applications, such as juices, wines, pretzels and biscuits it is sought to protect the contents against acquisition of undesirable flavors from the outside. Therefore, film structures which provide a harrier to oxygen, flavor/odor, grease/oil and moisture are highly desirable food packaging materials.

There is an ongoing trend to coat paper products with metalized films such as aluminum to provide moisture vapor and oxygen barrier protection. However, while these films provide good barrier properties, they limit the recyclability of the paper product. Development of low-carbon-footprint high harrier film materials in place of foil is increasingly needed.

To address this need, polymer-based film products such as ethylene vinyl alcohol, poly(vinyl) alcohol, and nylon prepared from m-xylene diamine are being used in today's food packaging market. These polymers possess high oxygen harrier properties but they have poor moisture harrier properties. In view of the foregoing limitations of known harrier films, there remains a need for barrier compositions which exhibit sufficient barrier properties in reducing the penetration of moisture and oxygen. The compositions and methods disclosed herein address these and other needs.

SUMMARY

Cellulose materials and methods of preparing the cellulose materials are disclosed herein. The cellulose material can be derived from a cotton fiber such as a cotton fabric, including post-consumer waste cotton fabrics. The method of preparing the cellulose material can include contacting the cotton liner or fabric with an oxidizing system to obtain an oxidized cotton material. The cotton fabric may be decolored, mechanically shredded, milled, or a combination thereof, prior to contacting it with the oxidizing system.

Any suitable oxidizing system can be used for oxidizing the cotton fiber. In some examples, the oxidizing system can include an N-oxyl compound. Exemplary N-oxyl compounds include 2,2,6,6-tetramethylpiperidine-1-oxyl (TEMPO), 4-hydroxy-2,2,6,6-tetramethylpiperidine-1-oxyl (4-hydroxy TEMPO), a 4-hydroxy TEMPO derivative obtained by etherification or esterification of a hydroxyl group of 4-hydroxy TEMPO, a phthalimide-N-oxyl (PINO) radical, an aza-adamantane type nitroxy radical, or a mixture thereof. The oxidizing system can further include a secondary oxidant, such as a hypochlorite compound. In some embodiments, the oxidizing system can include an aqueous mixture of the N-oxyl compound and a hypochlorite compound. During oxidation of the cotton fiber, the pH of the aqueous mixture can be maintained at from 8.5 to 11, such as at pH 10.

The method of preparing the cellulose materials can include processing the oxidized cotton material to form the cellulose material. Processing the oxidized cotton material can include filtering, neutralizing, evaporating, distilling, rinsing, casting, extruding, spinning, or a combination thereof.

Cellulose products can be formed from the cellulose materials described herein. For example, an active ingredient can be incorporated into the cellulose material to confer a suitable property to the cellulose material. In some examples, the cellulose product can be a packaging material, a biomedical device or implant, a drug delivery material, a fiber, a textile material, a template for electronic components, or a separation membrane. Methods of preparing the cellulose product can include dissolving or suspending an active ingredient in the cellulose material to form the cellulose product. The active ingredient can be selected from an inorganic nanoparticle, a therapeutic agent, and a combination thereof. The active ingredient can be present in an amount of from 0.01% to 20% by weight, based on the weight of the cellulose product.

In some examples, the cellulose product can be a food packaging material. The food packaging material can include the cellulose material and a nanoparticle active ingredient. In some cases, the nanoparticle active ingredient can exhibit moisture barrier properties, oxidation barrier properties, or a combination thereof. Examples of suitable nanoparticle active ingredient can include a silicon oxide nanoparticle, a silver nanoparticle, a cerium oxide nanoparticle, a zinc oxide nanoparticle, a poly(vinyl) alcohol nanoparticle, or a combination thereof. The food packaging material can have a moisture vapor transmission rate (MVTR) of 1.0 $g/m^2$ per 24 hours when measured at 38° C. and 90 RH %. Additionally, the food packaging material coated with the cellulose product can have an oxygen transmission rate (OTR) of 10 $cm^3/m^2$ per 24 hours when measured at 23° C., 0% RH, and 1 atm.

In some examples, the cellulose product can be a textile material. The textile material can include the cellulose material and nanoparticles that can impart a functionality selected from insulating finishing, electrical conductivity, hydrophobic finishing, waterproof finishing, soil repellent finishing, fire resistance finishing, wrinkle free finishing, anti-UV finishing, antimicrobial finishing, antistatic finishing, coloration, reflective finishing, sunblock finishing, fragrance finishing, fabric softening finishing, anti-oxidant finishing, or combinations thereof. Examples of suitable nanoparticles for use in the textile material can include nanoparticles as described herein, such as a silicon oxide nanoparticle, a silver nanoparticle, a cerium oxide nanoparticle, a zinc oxide nanoparticle, a poly(vinyl) alcohol nanoparticle, or a combination thereof.

Cellulose articles can be prepared from the cellulose materials described herein. Methods for recovering a cellulose article from the cellulose material can include casting, extruding, or spinning the cellulose material to form the cellulose article.

DETAILED DESCRIPTION

Provided herein are compositions and articles comprising cellulose materials. The compositions and articles comprising the cellulose materials can also include an active ingredient. Methods of making and using the compositions and articles are also described herein.

The compositions, articles, and methods described herein can be understood more readily by reference to the following detailed description of specific aspects of the disclosed subject matter and the Example included therein. However, before the present compositions and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

General Definitions

In this specification and in the claims that follow, reference will be made to a number of terms, which shall be defined to have the following meanings:

The term "fabric" as used herein refers to a web having a structure of individual fibers or threads which are interlaid by weaving (woven), knitting, braiding, or in an irregular, non-repetitive manner (non-woven). A nonwoven fabric or web can be formed from for example, melt-blowing processes, spun-bonding processes, and bonded carded web processes.

Throughout this specification the word "comprise" and other forms of the word, such as "comprising" and "comprises," means including but not limited to, and is not intended to exclude, for example, other additives, components, integers, or steps. The terms "include" and other forms of "include" has the same meaning as "comprise" and its other firms.

The singular forms "a," "an," and "the" include plural referents unless the context clearly dictates otherwise. Thus, for example, reference to "a composition" includes mixtures of two or more such compositions and reference to "the compound" includes mixtures of two or more such compounds, and the like.

"Optional" or "optionally" means that the subsequently described event or circumstance can or cannot occur, and that the description includes instances where the event or circumstance occurs and instances where it does not.

A weight percent (wt %) of a component, unless specifically stated to the contrary, is based on the total weight of the formulation or composition in which the component is included.

Reference will now be made in detail to specific aspects of the disclosed materials, compounds, compositions, articles, and methods, examples of which are illustrated in the accompanying Example.

Compositions

Provided herein are compositions and articles comprising cellulose materials. The cellulose materials can be derived from a natural cotton fiber or a cotton fabric. Cotton fabrics are known in the art and can include denim, terry, corduroy, flannel, canvas, and twill. In some cases, the cotton fabric can be derived from a pre-consumer or post-consumer cotton waste such as jeans or towels. Pre-consumer jeans manufacturing clippings or rags are available from the "jeans industry." the jeans comprising long cotton fibers, the length of which are in the range of 20 to 50 mm and the fineness of which are in the range of 10 to 20 µm.

The cellulose material can be formed into cellulose products. The cellulose products can include the cellulose material and an active ingredient that confers a suitable property to the cellulose product. For example, the cellulose product can include an active ingredient selected from an inorganic nanoparticle, a therapeutic agent, or a combination thereof. In some embodiments, the cellulose product can be a packaging material, a biomedical device or implant, a drug delivery material, a fiber, a textile material, a template for electronic components, or a separation membrane.

The active ingredient can be present in the cellulose product in an amount of 0.01% or greater by weight of the cellulose product. For example, the cellulose product can comprise 0.1% or greater, 0.1% or greater, 0.1% or greater, 0.2% or greater, 0.5% or greater, 1% or greater, 1.5% or greater, 2% or greater, 3% or greater, 4% or greater, 5% or greater, 6% or greater, 7% or greater, 8% or greater, 9% or greater, 10% or greater, 12% or greater, 15% or greater, 20% or greater, or 25% or greater of the active ingredient, based on the weight of the cellulose product. In some examples, the cellulose product can comprise 25% or less, 20% or less, 15% or less, 12% or less, 10% or less, 9% or less, 8% or less, 7% or less, 6% or less, 5% or less, 4% or less, 3% or less, 2.5% or less, 2% or less, 1.5% or less, 1% or less, 0.5% or less by weight active ingredient, based on the weight of the cellulose product. The amount of active ingredient in the cellulose product can range from any of the minimum values described above to any of the maximum values described above. For example, the amount of active ingredient in the cellulose product can range from 0.01% to 25%, 0.01% to 20%, 0.01% to 15%, 0.01% to 10%, 0.01% to 5%, 0.5% to 10%, 0.5% to 5%, 0.5% to 2.5%, 1% to 10%, or 1% to 5% by weight, based on the weight of the cellulose product.

Suitable examples of active ingredients useful in the cellulose products disclosed herein include an insulating material, an electrically conductive material (such as an antistatic material), a hydrophobic material, a fire retardant or suppressant, a water repellent material, a soil repellent material, a reflective material (such as a metallic reflector), a magnetic material, a thermochromic material, a bioactive agent (such as an anti-microbial agent, anti-fungal agent, or an insect repellent), a sunblock agent, a dye, a pigment, a fragrance, an insect repellent, a fabric softener, an anti-wrinkle material, a UV-protective material, an oxidation resistant material, or a combination thereof.

In some embodiments, the active ingredient can include a nanoparticle. The term "nanoparticle" as used herein, refers to any structure with one or more nanosized features. A nanosized feature can be any feature with at least one dimension less than 1 µm in size. The nanoparticle can have any of a wide variety of shapes including for example, spheroidal and elongated nanostructures. Thus, the term nanoparticle includes nanowires, nanotubes, spheroidal nanoparticles, and the like, or combinations thereof. The nanoparticles used herein can have an average diameter of 900 nanometers (nm) or less. In some embodiments, the average diameter of the nanoparticle can be 800 nm or less, 700 nm or less, 600 nm or less, 500 nm or less, 450 nm or less, 400 nm or less, 350 nm or less, 300 nm or less, 250 nm or less, 200 nm or less, 150 nm or less, 100 nm or less, or 50 nm or less. In some embodiments, the average diameter of the nanoparticle can be 5 nm or greater, 50 nm or greater, 100 nm or greater, 150 nm or greater, 200 nm or greater, 250 nm or greater, 300 nm or greater, 350 nm or greater, 400 nm or greater, 450 nm or greater, 500 nm or greater, 600 nm or greater, 700 nm or greater, 800 nm or greater, or 900 nm or greater. The average diameter of the nanoparticle can range from any of the minimum values described above to any of the maximum values described above. For example, the average diameter of the nanoparticle can range from 5 nm to 700 nm, from 5 nm to 500 nm, from 50 nm to 500 nm, or from 50 nm to 250 nm.

Examples of suitable nanoparticles for use in the cellulose product can include aluminum, iron, silver, cerium, zinc, gold, copper, cobalt, nickel, platinum, manganese, rhodium, ruthenium, palladium, titanium, vanadium, chromium, molybdenum, cadmium, mercury, calcium, zirconium, iridium, silicon, an oxide thereof, zeolite, graphite, carbon nanotubes, or a combination thereof. Specific examples can include silicon oxide nanoparticles, silver nanoparticles, cerium oxide nanoparticles, zinc oxide nanoparticles, polyvinyl alcohol nanoparticles, or combinations thereof. The nanoparticles described herein can be encapsulated within the cellulose material, dispersed throughout the cellulose material, or form a layer/coating on the cellulose material.

In some embodiments, the cellulose product can be a food packing material. In these embodiments, a nanoparticle that can exhibit moisture barrier properties, oxygen barrier properties, or a combination thereof, can be included in the cellulose material. In some examples, the cellulose product can be a textile material. The textile material can include any one of the active ingredients described herein.

Methods

Methods of making the cellulose materials and compositions containing the cellulose materials are also described herein. As described herein, the cellulose material may be derived from a cotton fiber or cotton fabr10046ic. The method can include cutting, mechanically shredding, and/or milling the cotton fabric to provided finely divided cotton fabrics. Any suitable device can be used to cut, shred, and/or mill the cotton fabric.

The method of making the cellulose material can include contacting the cotton fabric with an oxidizing system to obtain an oxidized cotton material. The oxidizing system can include an N-oxyl compound. Suitable N-oxyl compounds include 2,2,6,6-tetramethylpiperidine-1-oxyl (TEMPO), 4-hydroxy-2,2,6,6-tetramethylpiperidine-1-oxyl (4-hydroxy TEMPO), a 4-hydroxy TEMPO derivative obtained by etherification or esterification of a hydroxyl group of 4-hydroxy TEMPO, a phthalimide-N-oxyl (PINO) radical, an aza-adamantane type nitroxy radical, or a mixture thereof. Other suitable N-oxyl compounds include 4-oxo-2,2,6,6-tetramethyl-1-piperidinyloxy (4-oxo-TEMPO), 4-amino-2,2,6,6-tetramethylpiperidine-1-oxyl (4-amino-TEMPO), 4-acetamido-2,2,6,6-tetramethylpiperidine-1-oxyl (4-acetamido-TEMPO), 4-benzyloxy-2,2,6,6-tetramethylpiperidine-1-oxyl (4-benzyloxy-TEMPO), and 4-acetoxy-2,2,6,6-tetramethylpiperidine-1-oxyl (4-acetoxy-TEMPO), 4-phosphonooxy-TEMPO, N-hydroxybenzotriazole, or a mixture thereof.

The N-oxyl compound in the oxidizing system can be present in an amount of at least 0.1 mmol per gram of the cotton fabric. In some embodiments, the N-oxyl compound can be present in an amount of 0.15 mmol or greater or 0.2 mmol or greater per gram of the cotton fabric. In some embodiments, the N-oxyl compound can be present in an amount of 0.25 mmol or less, 0.2 mmol or less, or 0.15 mmol or less per grain of the cotton fabric. In some embodiments, the N-oxyl compound can be present in an amount of from 0.1 mmol to 0.25 mmol or from 0.15 mmol to 0.20 mmol per gram of the cotton fabric. In some embodiments, the N-oxyl compound can be present in a catalytic amount for oxidation of the cotton fabric.

The oxidizing system can include a secondary oxidant. Suitable secondary oxidants can include a hypochlorite compound such as sodium hypochlorite or tert-butyl hypochlorite, sodium chlorite, (diacetoxyiodo)benzene, meta-chloroperoxybenzoic acid, calcium chlorite, sodium bromite, chlorine, bromine, trichloroisocyanuric acid, or a combination thereof.

The secondary oxidant, such as sodium hypochlorite can be present in an amount of at least 3 mmol per gram of the cotton fabric. In some embodiments, the secondary oxidant can be present in an amount of 4 mmol or mater, 5 mmol or greater, 6 mmol or greater, 7 mmol or greater, 8 mmol or greater, 9 mmol or greater, 10 mmol or greater, 15 mmol or greater, or 20 mmol or greater per gram of the cotton fabric. In some embodiments, the secondary oxidant can be present in an amount of 25 mmol or less, 20 mmol or less, 15 mmol or less, 10 mmol or less, 9 mmol or less, 8 mmol or less, 7 mmol or less, 6 mmol or less, 5 mmol or less, or 4 mmol or less per gram of the cotton fabric. In some embodiments, the secondary oxidant can be present in an amount of from 3 mmol to 25 mmol or from 5 mmol to 15 mmol per gram of the cotton fabric.

In some embodiments, the oxidizing system can include an aqueous mixture of the N-oxyl compound and the secondary oxidant. For example, the oxidizing system can include an aqueous mixture of 4-hydroxy TEMPO, sodium hypochlorite, and sodium bromide.

The cotton fabric can be present in an amount of 50% or less by weight of the aqueous mixture. For example, the cotton fabric can be present in an amount of 35% by less, 25% by less, 10% by less, 5% by less, 3% by less, or 2% by less by weight of the aqueous mixture.

Oxidation of the cotton fabric can be controlled by maintaining the pH of the aqueous mixture from 8.5 to 11. In some cases, the pH of the aqueous mixture can be maintained at 10.

Any suitable compound can be used to adjust the pH of the aqueous mixture. In some embodiments, the pH can be adjusted using a base such as sodium hydroxide. Oxidation of the cotton fabric can also be controlled by heating the mixture comprising the cotton fabric and the oxidizing system.

In some cases, the method can include decoloring the cotton fabric prior to contacting the fabric with the oxidizing system. For example, where the cotton fabric is a post-consumer waste, such as a jeans, the method can include decoloring the cotton fabric prior to oxidation. In some embodiments, the method does not include decoloring the cotton fabric prior to contacting the fabric with the oxidizing system. In these embodiments, the cotton fabric can be decolored during oxidization of the cotton fabric.

Decoloring the cotton fabric can include contacting the cotton fabric with an oxidizing or reducing agent. Suitable oxidizing agents for decoloring the cotton fabric can include hypochlorite (for e.g. sodium hypochlorite), peroxide (such as hydrogen peroxide or benzoyl peroxide), sodium chlorite, potassium permanganate, or ozone. Suitable reducing agents for decoloring the cotton fabric can include sulfur dioxide, thiourea dioxide, sodium hydrosulfite, sodium hydroxymethanesulfinate, zinc formaldehyde sulfoxylate, calcium formaldehyde sulfoxylate, sodium sulfite, sodium bisulfite, and tin (II) chloride.

The oxidized cotton material can be processed to form the cellulose materials described herein. Processing the oxidized cotton material can include filtering (for example to separate insoluble cotton fabric), neutralizing, evaporating, distilling, rinsing/washing, casting, extruding, spinning, or a combination thereof, the mixture comprising the oxidized cotton material. In some embodiments, processing the oxidized cotton material can include neutralizing the aqueous mixture to a pH of about 7. For example, the method can include rinsing the oxidized cotton material with a solvent, such as water until the filtrate solution is neutral.

As described herein, the cellulose material can be used to form a cellulose product. The method of limning the cellulose product can include dispersing, such as by homogenizing the cellulose material into a medium comprising a solvent. The solvent can include be any suitable solvent such as water, an alcohol, or an ionic liquid. Optionally, the medium can be filtered to remove insoluble fractions of cellulose material. The method can further include dissolving and/or suspending one or more active ingredients in the medium comprising the cellulose material. The mixture of the cellulose material and active ingredient can be homogenized to form a viscous mixture. The homogenized mixture can be carted into a film by pouring into a container and drying at low temperature for example about 40'C. In some embodiments, the cellulose product can be obtained from extruding, spinning, or a combination thereof. For example, a cellulose product can be prepared from a spinning process such as a gap/dry-wet spinning process or by a wet-wet spinning process.

As described herein, the cellulose product can be a food packing material. The food packaging material can exhibit moisture barrier and oxygen barrier properties. The liquid-water and water-vapor resistance of the fool packaging material comprising the cellulose material can be tested with the Cobb method, described by TAPPI T 441 (2001), which is incorporated by reference herein in its entirety. This method determines the amount of liquid water or moisture vapor absorbed by the cellulose material in a specified time under standardized conditions. In some embodiments, the food packaging product comprising the cellulose material described herein would pass the water resistance test set forth in this test method.

In some embodiments, the food packaging material comprising the cellulose material can exhibit a Cobb value of 0.01 $g/m^2$ to 25 $g/m^2$ (e.g., 25 $g/m^2$ or less, 20 $g/m^2$ or less, 15 $g/m^2$ or less, 10 $g/m^2$ or less, or 5 $g/m^2$ or less). In some embodiments, the food packaging material can exhibit a moisture vapor transmission rate (MVTR) of 1 $g/m^2$ or less per 24 hours when measured at 38° C. and 90 RH %. For example, the food packaging material can exhibit a moisture vapor transmission rate of 0.5 $g/m^2$ or less or 0.3 $g/m^2$ or less. In some embodiments, the food packaging material comprising the cellulose material can exhibit an oxygen transmission rate (OTR) of 10 $cm^3/m^2$ or less per 24 hours when measured at 23° C., 0 RH %, and 1 atm. For example, the food packaging material can exhibit an oxygen transmission rate of 8 $cm^3/m^2$ or less, 6 $cm^3/m^2$ or less, 5 $cm^3/m^2$ or less, 4 $cm^3/m^2$ or less, 3 $cm^3/m^2$ or less, 2 $cm^3/m^2$ or less, or 1 $cm^3/m^2$ or less per 24 hours when measured at 23° C. 0 RH %, and 1 atm. The moisture vapor transmission rate (MVTR) can be determined as described in ASTM E398, ASTM F1249 or TAPPI T448-M49. In some examples, the moisture vapor transmission rate (MVTR) can be determined as described in ASTM E398. The oxygen transmission rate (OTR) can be determined as described in ASTM D3985 or ASTM F1927. In some examples, the oxygen transmission rate (OTR) can be determined as described in ASTM D3985.

In some examples, the cellulose product can be a textile material. The textile material can include an active ingredient such that it can exhibit an insulating property, an electrically conductive property (such as an antistatic property), a hydrophobic property, a fire retardant or suppressant property, a water repellent property, a soil repellent property, a reflective property, a magnetic property, a thermochromic property, a bioactive property, a sunblock property, a fragrance, an insect repellent property, a fabric softening property, an anti-wrinkle property, a UV-protective property, an oxidation resistant property, or a combination thereof. In some examples, the textile material can be thermally insulating. The basis weight of the textile material can be 20 $g/m^2$ or greater. For example, the basis weight of the textile material can be 25 $g/m^2$ or greater, 30 $g/m^2$ or greater, 35 $g/m^2$ or greater, 40 $g/m^2$ or greater, 45 $g/m^2$ or greater, 50 $g/m^2$ or greater, 55 $g/m^2$ or greater, 60 $g/m^2$ or greater, 65 $g/m^2$ or greater, 70 $g/m^2$ or greater, 80 $g/m^2$ or greater, 90 $g/m^2$ or greater, 100 $g/m^2$ or greater, 110 $g/m^2$ or greater, 140 $g/m^2$ or greater, 150 $g/m^2$ or greater, 170 $g/m^2$ or greater, 180 $g/m^2$ or greater, 190 $g/m^2$ or greater, or 200 $g/m^2$ or greater. In some examples, the basis weight of the textile material can be 200 $g/m^2$ or less. For example, the basis weight of the fabric can be 190 $g/m^2$ or less, 180 $g/m^2$ or less, 160 g/m or less, 150 $g/m^2$ or less, 130 $g/m^2$ or less, 110 $g/m^2$ or less, 100 $g/m^2$ or less, 90 $g/m^2$ or less, 80 $g/m^2$ or less, 70 g/m or less, 65 $g/m^2$ or less, 60 $g/m^2$ or less, 55 $g/m^2$ or less, 50 $g/m^2$ or less, 45 $g/m^2$ or less, 40 $g/m^2$ or less, 35 $g/m^2$ or less, 30 $g/m^2$ or less, or 25 $g/m^2$ or less. The basis weight of the textile material can range from any of the minimum values described above to any of the maximum values described above. For example, the basis weight of the textile material can range from 25 $g/m^2$ to 200 $g/m^2$, from 50 $g/m^2$ to 200 $g/m^2$, or from 50 $g/m^2$ to 170 $g/m^2$. The textile material can be made into textiles including jackets, coats, skirts, pants, suits, slacks, vests, gloves, and the like. The fabrics can also be made into use in non-apparel applications such as furniture and carpets.

EXAMPLES

Example 1: Preparation of Recycled Cotton Nanofiber Film

A piece of towel fabric (0.5 g) was cut, ground, and suspended in a solution system containing water (25 mL), 4-hydroxyl-TEMPO (0.008 g, 0.04 mmol), and sodium bromide (0.05 g, 0.5 mmol). TEMPO-mediated oxidation of the fabric slurry was started by adding 5% NaClO solution (10 mmol of NaClO per gram of cellulose) dropwise with gentle agitation at room temperature. The oxidation was controlled by maintaining the pH value at 10 by adding 0.5 M NaOH. When no more decrease in pH was observed, the reaction was taken as finished. The NaClO-oxidized cellulose (NOC) was thoroughly washed with distill water until the filtrate solution was neutral.

To make cellulose nanofibers, 0.2 g NOC was dispersed in 200 mL water (0.1 wt % of NOC concentrations) at room temperature and mechanically agitated for 10 minutes using a planetary mixer at a low rotation rate. The insoluble fractions were removed from the dispersion by filtration. The cellulose dispersion was homogenized for 3 h in the mixer with a high rotation rate to produce a viscous NOC nanofiber suspension, by adding 1 wt % $SiO_2$ nanoparticle. A NOC nanofiber film was formed by a casting method. The nano-dispersion was poured into a 4×4 inch plastic dish for drying for 24 h at 40° C.

It will be apparent to those skilled in the an that various modifications and variations can be made in the present disclosure without departing from the scope or spirit of the invention. Other embodiments of the disclosure will be apparent to those skilled in the an from consideration of the specification and practice of the methods disclosed herein. It is intended that the specification and examples be considered as exemplary only, with a true scope and spirit of the invention being indicated by the following claims.

What is claimed is:

1. A method of making a cellulose product, the method comprising:

contacting a cotton fabric with an oxidizing system to obtain an oxidized cotton material, wherein the cotton fabric is derived from a post-consumer cotton waste and the oxidizing system comprises an N-oxyl compound;

processing the oxidized cotton material to form a cellulose material; and dissolving or suspending an active ingredient in the cellulose material to form the cellulose product;

wherein the active ingredient comprises an inorganic particle having moisture barrier properties, oxidation barrier properties, or a combination thereof;

wherein the inorganic particle comprises a silicon oxide nanoparticle, a cerium oxide nanoparticle, or a combination thereof; and wherein the active ingredient is present in an amount of from 0.01% to 20% by weight, based on the weight of the cellulose product.

2. The method of claim 1, wherein the cotton fabric is mechanically shredded, milled, or a combination thereof, prior to contacting the cotton fabric with the oxidizing system.

3. The method of claim 1, wherein the N-oxyl compound is selected from 2,2,6,6-tetramethylpiperidine-1-oxyl (TEMPO), 4-hydroxy-2,2,6,6-tetramethylpiperidine-1-oxyl (4-hydroxy TEMPO), a 4-hydroxy TEMPO derivative obtained by etherification or esterification of a hydroxyl group of 4-hydroxy TEMPO, a phthalimide-N-oxyl (PINO) radical, an aza-adamantane type nitroxy radical, or a mixture thereof.

4. The method of claim 1, wherein the oxidizing system comprises an aqueous mixture of the N-oxyl compound and a hypochlorite compound.

5. The method of claim 4, wherein the pH of the aqueous mixture is maintained at from 8.5 to 11.

6. The method of claim 1, further comprising decoloring the cotton fabric prior to contacting the cotton fabric with the oxidizing system.

7. The method of claim 1, wherein processing the oxidized cotton material comprises filtering, neutralizing, evaporating, distilling, rinsing, casting, extruding, spinning, or a combination thereof.

8. The method of claim 1, wherein the method further comprises dissolving or suspending an additional inorganic nanoparticle, a therapeutic agent, or a combination thereof in the cellulose material, such that the cellulose product further comprises the additional inorganic nanoparticle and/or the therapeutic agent.

9. The method of claim 8, wherein the additional inorganic nanoparticles and/or therapeutic agent impart a functionality selected from insulating finishing, electrical conductivity, hydrophobic finishing, waterproof finishing, gas barrier, soil repellent finishing, fire resistance finishing, wrinkle free finishing, anti-UV finishing, antimicrobial finishing, antistatic finishing, coloration, reflective finishing, sunblock finishing, fragrance finishing, fabric softening finishing, anti-oxidant finishing, or combinations thereof.

10. The method of claim 1, wherein the method further comprises dissolving or suspending a silver nanoparticle, a zinc oxide nanoparticle, a polyvinyl alcohol nanoparticle, or a combination thereof in the cellulose material, such that the cellulose product further comprises the silver nanoparticle, the zinc oxide nanoparticle, the polyvinyl alcohol nanoparticle, or a combination thereof.

11. The method of claim 1, wherein the active ingredient includes the silicon oxide nanoparticle.

12. The method of claim 1, wherein the oxidizing system comprises an aqueous mixture of the N-oxyl compound and a secondary oxidant, wherein the aqueous mixture is maintained at a pH from 8.5 to 11, and wherein the secondary oxidant includes a hypochlorite compound, (diacetoxyiodo) benzene, meta-chloroperoxybenzoic acid, calcium chlorite, sodium bromite, chlorine, bromine, trichloroisocyanuric acid, or a combination thereof.

13. The method of claim 1, wherein the active ingredient is present in an amount of from 0.5% to 20% by weight, based on the weight of the cellulose product.

14. The method of claim 1, wherein the active ingredient is present in an amount of from 0.01% to 2% by weight, based on the weight of the cellulose product.

* * * * *